US00PP15188P2

(12) United States Plant Patent
Talmadge

(10) Patent No.: US PP15,188 P2
(45) Date of Patent: Sep. 28, 2004

(54) **INTERSPECIFIC *DIASCIA* PLANT NAMED 'BALWHISWHIT'**

(50) Latin Name: *Diascia hybrid*
Varietal Denomination: Balwhiswhit

(75) Inventor: Paul A. Talmadge, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 30 days.

(21) Appl. No.: 10/734,558

(22) Filed: Dec. 12, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Wood, Phillips, Katz, Clark & Mortimer

(57) ABSTRACT

A new and distinct *Diascia* plant named 'Balwhiswhit' characterized by its white-colored flowers, medium green-colored foliage and a spreading and trailing growth habit.

1 Drawing Sheet

Latin name of genus and species of plant claimed: *Diascia hybrid.*
Variety denomination: 'Balwhiswhit'.

BACKGROUND OF THE INVENTION

The present invention comprises a new and distinct cultivar of Interspecific *Diascia* plant hereinafter referred to by the cultivar name 'Balwhiswhit'.

The new cultivar was developed by the inventor in a controlled breeding program during the summer of 2000, at Guadalupe, Calif. The objective of the breeding program was the development of *Diascia* cultivars with a well-branched, spreading growth habit, continuous flowering and medium green-colored foliage.

The female (seed) parent of 'Balwhiswhit' was the proprietary Interspecific *Diascia* selection designated '377-3' (not patented) characterized by its apricot-colored flowers, medium green-colored foliage and prostrate habit. The male (pollen) parent of 'Balwhiswhit' was the proprietary Interspecific *Diascia* selection designated '399-1' (not patented) characterized by its light lavender-colored flowers, light green-colored foliage, and spreading, mounded habit. Both parental cultivars have the following species in their background, *Diascia barbarae, Diascia integerimma*, and *Diascia mollis*. 'Balwhiswhit' was discovered and selected in the winter of 2000 as a single flowering plant from within the progeny of the above stated cross-pollination and was initially designated '601-1m-2-2'.

Asexual reproduction of the new cultivar by terminal stem cuttings taken since the winter of 2000 at Guadalupe, Calif. and West Chicago, Ill. has demonstrated that the new cultivar reproduces true to type with all the characteristics, as herein described, firmly fixed and retained through successive generations of such asexual propagation.

SUMMARY OF THE INVENTION

It has been repeatedly found that the cultivar of the present invention:

1. Exhibits white-colored flowers,
2. Forms medium green-colored foliage, and
3. Exhibits a spreading and trailing growth habit.

Plants of the new cultivar differ from plants of the female parent primarily in flower color, and from plants of the male parent primarily in flower color and foliage color.

Of the many *Diascia* cultivars know to the inventor, the most similar to 'Balwhiswhit' is the cultivar 'Iceburg' (not patented). However, in side-by-side comparisons, plants of 'Balwhiswhit' have larger flowers than plants of the cultivar 'Iceburg'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the values cited in the detailed description, which accurately describes the colors of 'Balwhiswhit'. The plants were grown for 10 weeks in a greenhouse at West Chicago, Ill.

DETAILED BOTANICAL DESCRIPTION

Figure 1:
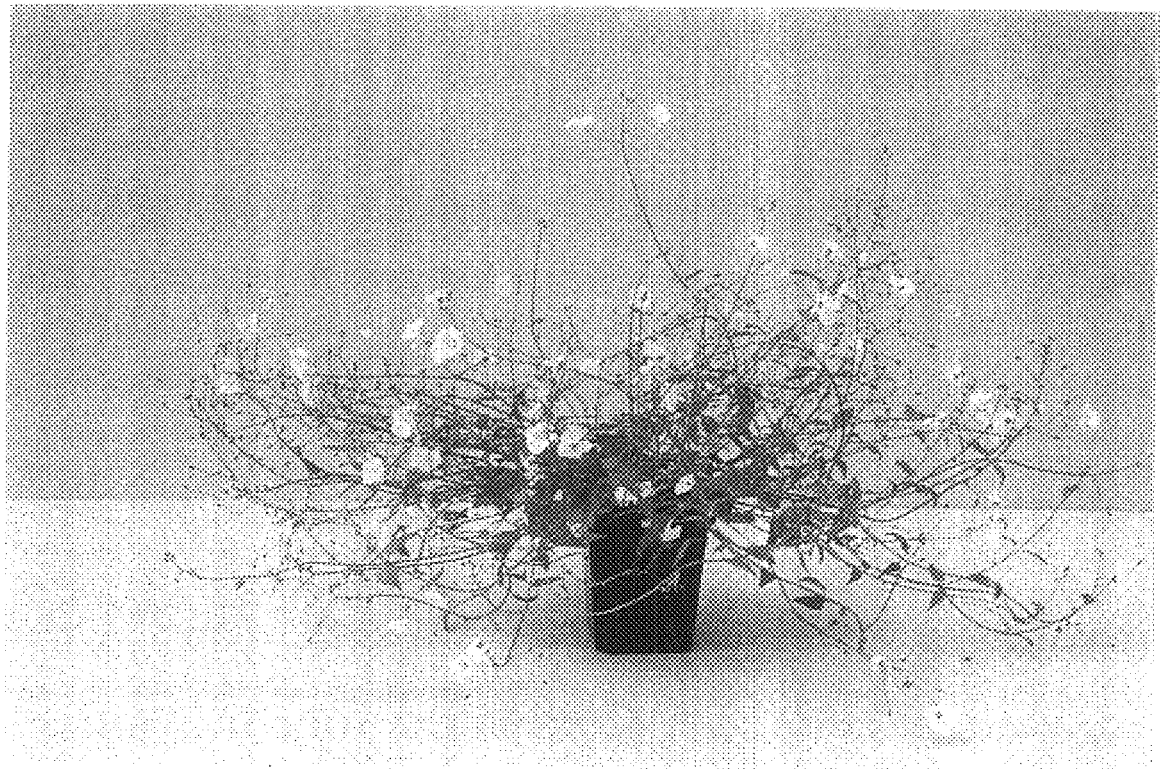
FIG. 1 illustrates a side view of the overall growth and flowering habit of 'Balwhiswhit'.
Figure 2:
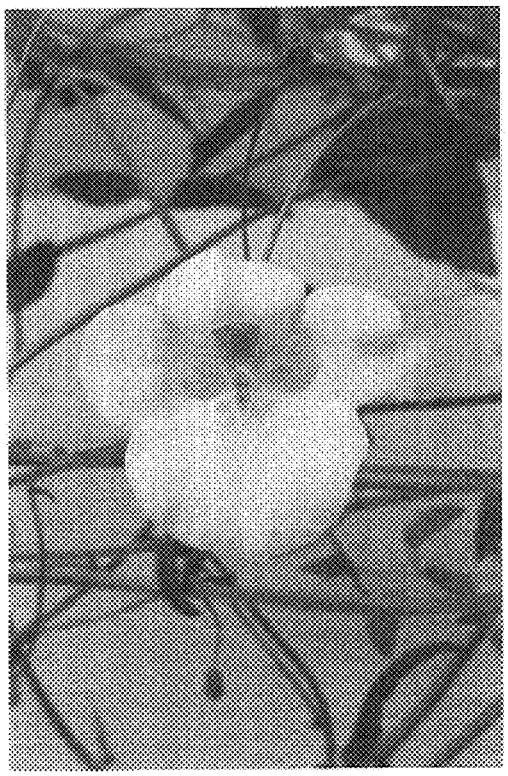
FIG. 2 illustrates a close-up view of an individual flower of 'Balwhiswhit'.

The new cultivar has not been observed under all possible environmental conditions to date. Accordingly, it is possible that the phenotype may vary somewhat with variations in the environment, such as temperature, light intensity, and day length. The chart used in the identification of colors described herein is the R.H.S. Colour Chart of The Royal Horticultural Society, London, England, 1995 edition, except where general color terms of ordinary dictionary significance are used. The color values were determined on Jul. 23, 2003. The readings were taken between 1:00 and 3:00 p.m. under natural light conditions. The plants were produced from terminal stem cuttings taken from stock plants and were grown in a double polycarbonate- covered greenhouse under conditions comparable to those used in commercial practice. The plants were grown in 10 cm pots for 10 weeks while utilizing a soilless growth medium. Greenhouse temperatures were maintained at approximately 62°–75° F. (17°–24° C.) during the day and approximately 52°–60° F. (11°–15° C.) during the night. Greenhouse light levels were maintained at 5,000 to 8,000 footcandles during the day.

Botanical Classification: Interspecific *Diascia* cultivar 'Balwhiswhit'.

Parentage:

*Female parent.*—Proprietary Interspecific *Diascia* selection designated '377-3', not patented.

*Male parent.*—Proprietary Interspecific *Diascia* selection designated '399-1', not patented.

Propagation:

*Type cutting.*—Terminal stem cutting.

*Time to initiate roots.*—Approximately 6 to 9 days.

*Time to form roots.*—Approximately 3 to 4 weeks.

*Root description.*—Fine, fibrous.

*Rooting habit.*—Freely branching.

Plant description:

*Crop time.*—Approximately 5 to 7 weeks from planting of a rooted cutting in a 10 cm pot.

*Habit of growth.*—Vigorous. Freely branching with branches forming at every node. A mature plant, 10 weeks after the planting of a rooted cutting, measures approximately 22.8 cm in height and approximately 57.4 cm in diameter (area of spread) with approximately 45 lateral flowering branches.

*Form.*—Spreading, trailing.

*Lateral branch.*—Shape: Square. Length: Approximately 32.4 cm. Diameter: Approximately 1.4 mm. Texture: Glabrous. Internode length at middle of branch: Approximately 3.7 cm. Color: Closest to 146A.

*Foliage.*—Type: Simple. Arrangement: Opposite. Shape: Ovate. Margin: Serrate. Apex: Acute. Base: Truncate. Texture of upper and lower surfaces: Glabrous. Quantity of leaves per lateral branch: Approximately 8. Leaf length: Approximately 2.9 cm. Leaf width: Approximately 1.5 cm. Leaf orientation to stem: Obtuse to parallel. Leaf fragrance: None. Venation pattern: Pinnate. Color of mature foliage: Upper surface: Slightly darker than 146A with venation of 146A. Lower surface: 148B with venation of 146A. Petiole length: Approximately 4 mm. Petiole diameter: Approximately 1 mm. Petiole texture: Upper and lower surfaces: Glabrous. Petiole color: 146C.

Flowering description:

*Flowering habit.*—Freely flowering.

*Natural flowering season.*—Year round in greenhouse environment and spring through autumn in outdoor garden.

*Flower arrangement.*—Terminal racemes.

*Raceme description.*—Length (depth): Approximately 6.6 cm. Width: Approximately 5.8 cm. Number of flowers per raceme: 5.2.

Flower description:

*Type.*—Solitary, not persistent, five lobed, zygomorphic, with two nectar spurs.

*Fragrance.*—None.

*Aspect.*—Concave.

*Lastingness of a single bloom.*—Approximately 5 days.

*Flower size.*—Width: Approximately 1.7 cm. Length: Approximately 1.9 cm. Depth: Approximately 4 mm.

*Petals.*—Number: Five. Type: Imbricate, fused at base. Aspect: Cupped. Margin: Entire. Apex: Obtuse. Appearance: Iridescent. Color: Upper and lower surfaces: N155D. Indentation at base of upper petals: Length: 3 mm. Width: 3 mm. Color: 6B.

*Two upper (banner) petals.*—Length: Approximately 6 mm. Width: Approximately 5 mm. Texture of upper and lower surface: Glabrous.

*Lateral petals.*—Length: Approximately 6 mm. Width: Approximately 7 mm. Texture of upper and lower surface: Glabrous. Sharply curved nectar spurs form at base of each of the lateral petals.

*Nectar spurs.*—Length: 6.1 mm. Diameter at base: 2 mm. Diameter at tip: 1 mm. Color: 2D with tip of 1D.

*Lower petal.*—Length: Approximately 1 cm. Width: Approximately 1.3 cm. Texture of upper surface: Glabrous except glandular where petals are fused. Gland color: 51A. Texture of lower surface: Glabrous.

*Sepals.*—Quantity: 5. Shape: Lanceolate. Length: Approximately 3 mm. Width: Approximately 1 mm. Apex: Acute. Margin: Entire. Upper surface of sepals is moderately glandular pubescent. Glands are colorless and translucent. Lower surface has no pubescence. Upper and lower surfaces are 137C. Calyx shape: Five pointed star. Calyx length: Approximately 3 mm. Calyx diameter: Approximately 6 mm.

*Peduncle.*—Length: Approximately 2 cm. Diameter: Approximately 1 mm. Aspect: At acute angle to stem. Texture: Moderately glandular pubescent. Glands are colorless and translucent. Color: 143C.

*Bud (at first color).*—Shape: Oval, flat. Length: Approximately 4.8 mm in length. Diameter: Approximately 7.5 mm. Color: 2C.

*Reproductive organs.*—Androecium: There are 4 stamens per flower. Filament length: 4 mm. Filament color: 2D. Anther shape: Oval. Anther length: 3 mm. Anther color: 13B. Pollen amount: Abundant. Pollen color: 13A. Gynoecium: Pistil number: One per flower. Pistil length: 4 mm. Stigma shape: Round. Stigma length: 0.5 mm. Stigma color: N144D. Style length: Approximately 1.5 mm. Style color: 154D. Ovary length: Approximately 2 mm. Ovary color: N144D.

Seed and fruit production: Neither seed nor fruit production has been observed.

Disease and pest resistance: Resistance to pathogens or pests common to *Diascia* has not been observed.

Hardiness zone: 'Balwhiswhit' is hardy in zones nine (9) and above.

What is claimed is:

1. A new and distinct cultivar of Interspecific *Diascia* plant named 'Balwhiswhit' substantially as herein shown and described, which:

1. Exhibits white-colored flowers,
2. Forms medium green-colored foliage, and
3. Exhibits a spreading and trailing growth habit.

* * * * *